US012103900B2

(12) United States Patent
Goenka et al.

(10) Patent No.: US 12,103,900 B2
(45) Date of Patent: Oct. 1, 2024

(54) ENVIRONMENT-FRIENDLY PROCESS FOR SELECTIVE ACYLATION OF AMINOPHENOL

(71) Applicant: LAXMI ORGANIC INDUSTRIES LTD, Mumbai (IN)

(72) Inventors: Ravi Goenka, Mumbai (IN); Ajay A Audi, Mumbai (IN)

(73) Assignee: LAXMI ORGANIC INDUSTRIES LTD, Mumbai (IN)

( * ) Notice: Subject to any disclaimer, the term of this patent is extended or adjusted under 35 U.S.C. 154(b) by 219 days.

(21) Appl. No.: 17/904,981

(22) PCT Filed: Nov. 11, 2021

(86) PCT No.: PCT/IN2021/051062
§ 371 (c)(1),
(2) Date: Aug. 25, 2022

(87) PCT Pub. No.: WO2022/113098
PCT Pub. Date: Jun. 2, 2022

(65) Prior Publication Data
US 2023/0104724 A1   Apr. 6, 2023

(30) Foreign Application Priority Data
Nov. 24, 2020  (IN) .............................. 202021051134

(51) Int. Cl.
*C07C 221/00*   (2006.01)
(52) U.S. Cl.
CPC ................................ *C07C 221/00* (2013.01)
(58) Field of Classification Search
None
See application file for complete search history.

(56) References Cited

U.S. PATENT DOCUMENTS 3,113,150 A * 12/1963 Young ................... C07C 233/16
564/216
3,574,743 A *  4/1971 Coupland ............... C10M 1/08
564/402
4,524,217 A *  6/1985 Davenport ............ C07C 233/16
564/223
5,399,760 A *  3/1995 Zey ........................ C07C 231/24
564/216

FOREIGN PATENT DOCUMENTS

| CN | 103508916 A * | 1/2014 | |
| CN | 104447387 A | 3/2015 | |
| EP | 2649993 A1 | 10/2013 | |
| WO | 1994025428 A1 | 11/1994 | |
| WO | WO-9425428 A1 * | 11/1994 | ........... C07C 231/24 |
| WO | 2017154024 A1 | 9/2017 | |

OTHER PUBLICATIONS

G. Moss et al., 67 Pure & Applied Chemistry, 1307-1375 (1995) (Year: 1995).*
Hawley's Condensed Chemical Dictionary, pp. 26, 273-275 (16th ed., 2016, R.J. Larrañaga ed.) (Year: 2016).*
G. Solomons, Organic Chemistry, 645-647 (5th ed., 1992) (Year: 1992).*
I. Calder et al., 32 Australian Journal of Chemistry, 1301-1306 (1979) (Year: 1979).*
T. Tidwell, 23 Science of Synthesis, 15-51 (2006) (Year: 2006).*
C. Sivaraj et al., Chemistry, an Asian Journal, 2773-3794 (2021) (Year: 2021).*
G. Brahmachari et al., 49B Indian Journal of Chemistry, 1274-1281 (2010) (Year: 2010).*
International Search Report from PCT/IN2021/051062 Jan. 31, 2022, 3 pgs.
Brahmachari, et al., A Green Approach to Chemoselective N-acetylation 1-10 of Amines Using Catalytic Amount of Zinc Acetate in Acetic Acid Under Microwave Irradiation, Indian Journal of Chemistry, vol. 49B, Sep. 2010, pp. 1274-1281.
Henry, et al., Generation and Trapping of Ketenes in Flow, Eur. 1-10 J. Org. Chem. 2015, 1491-1499, DOI: 10.1002/ejoc.201403603.

* cited by examiner

*Primary Examiner* — Alexander R Pagano

(74) *Attorney, Agent, or Firm* — Locke Lord LLP; Tim Tingkang Xia, Esq.

(57) ABSTRACT

The present invention relates to an environment-friendly process for selective acylation of aminophenol. In particular, the present invention relates to an environment-friendly process for selective acylation of para-aminophenol to obtain N-acetyl-para-aminophenol (APAP).

10 Claims, No Drawings

ENVIRONMENT-FRIENDLY PROCESS FOR SELECTIVE ACYLATION OF AMINOPHENOL

FIELD OF THE INVENTION

The present invention relates to an environment-friendly process for selective acylation of aminophenol. In particular, the present invention relates to an environment-friendly process for selective acylation of para-aminophenol to obtain N-acetyl-para-aminophenol (APAP).

BACKGROUND OF THE INVENTION

Acylation of aminophenol is usually carried out using a suitable combination of acylation reagents and catalysts. The most common acylation product of aminophenol is acetaminophen. Acetaminophen is popularly known as paracetamol or N-acetyl-para-aminophenol (APAP). Paracetamol is a pharmaceutical agent that relieves pain and reduces fever and is one of the world's most used analgesics.

The state-of-the-art or commercially used processes for paracetamol synthesis use various acylation reagents. Acetic anhydride is one such widely used acylation reagent, wherein the acylation reaction is carried out in the presence of concentrated sulfuric acid. Other similar reagents used in the art include, such as but not limited to, acetic acid and acetyl chloride. These reagents have several limitations of their own—one of the major limitations being the strict regulation on their usage in several countries. For instance, acetic anhydride is a hazardous substance and being used in narcotics and therefore, regulated in countries like US and India. Another major limitation is the generation of hydrochloric acid and acetic acid as by product, which are troublesome effluents. Particularly, the generation of acetic acid is generally in equimolar amounts and gets diluted in water, thereby increasing the cost incurred in recovering the same. A major challenge associated with the formation of hydrochloric acid is the corresponding salt formation, the mitigation of which remains a challenge. Furthermore, this process is relatively complex requiring a fair number of reaction and purification steps. Moreover, the acylation step in the process gives rise to various problems, such as the difficulty of monoacetylating the hydroxy aromatic amine, oligomerization of the hydroxy aromatic amine and colour body formation etc.

U.S. Pat. No. 4,524,217 B1 relates to the production of N-acyl-hydroxy aromatic amine, e.g. N-acetyl-para-aminophenol (APAP) from hydroxy aromatic ketones, e.g. 4-hdyroxyacetophenone. The maximum yield of APAP reported is approx. 89%. The process disclosed here makes use of acetic acid and acetic anhydride as acylating agents.

U.S. Pat. No. 4,607,125 A1 discloses that hydroxy aromatic ketones, such as 4-hydroxyacetophenone, are useful in the production of APAP. Acylation is accomplished by reacting phenol with an acylating agent such as acetic anhydride in the presence of a Friedel-Crafts type catalyst such as aluminium chloride, hydrogen fluoride (HF) or boron trifluoride ($BF_3$).

U.S. Pat. No. 5,221,769 discloses a process for producing APAP which comprises isomerizing p-aminophenyl acetate in the presence of an acid, preferably acetic acid. The maximum yield of APAP is reported approx. 99%, however, the purity is considerably low.

US20040138509 A1 discloses a process of producing organic compounds, such as acetaminophen, nitroalcohols and indoles, using a catalyst system of an oxyethylene ether and a metal containing inorganic or organic reagent. APAP is obtained by amidation/reduction reaction and the maximum yield reported is approx. 80%.

Thus, there is a need for a process which is environment-friendly, less complex, economical and results in APAP in a higher yield and purity, while at the same time minimizing and eliminating the generation of hazardous substances and troublesome effluents.

SUMMARY OF THE INVENTION

In one aspect, the present invention provides an environment-friendly process for selective acylation of aminophenol comprising the step of reacting an aqueous solution of the aminophenol and a ketene in presence of a catalyst and a stabilizer.

DESCRIPTION OF THE INVENTION

The present invention provides an environment-friendly process for selective acylation of aminophenol comprising the step of reacting an aqueous solution of the aminophenol and a ketene in presence of a catalyst and a stabilizer.

In the present context, "environment-friendly" refers to the process being capable of substantially reducing the requirement of recovering the hazardous and troublesome effluents in comparison with the state-of-the-art or commercially used processes. In particular, the requirement of recovering the hazardous and troublesome effluents, such as but not limited to acetic acid, is significantly low. Said otherwise, in the state-of-the-art or commercially used processes the acetic acid generated during the first batch (after acylation reaction using acetic anhydride) is more than 20 wt. % which requires immediate recovery of the acetic acid. In fact, every batch requires to be sent for recovery, thereby resulting in lower yield of the final product. The amount of acetic acid generated in the present invention, on the other hand, is as low as one tenth of that of the state-of-the-art or commercially used processes. Hence, significantly lesser number of recovery steps are required, thereby resulting in an increase in the yield and selectivity of the final product.

The present invention is also advantageous in the sense that the impurities are also reduced after every recycling, as described hereinbelow. For every recycling of mother liquor, the impurities which are soluble in the acetic acid are removed and hence, the product yield and purity is increased. Finally, when the concentration of acetic acid in the mother liquor reaches the optimum level which is obtained after the first batch of the commercially used processes, the mother liquor is sent to the recovery step. Suitable recovery means for recovering acetic acid are well known to a person skilled in the art.

In the present context, aminophenol refers to three isomeric chemical compounds viz. 2-aminophenol, 3-aminophenol and 4-aminophenol. These isomeric compounds are alternatively referred as o-aminophenol, m-aminophenol and p-aminophenol, respectively. Herein, o-, m- and p-aminophenol refers to ortho-, meta- and para-aminophenol, respectively.

The aminophenol can be selected from one or more than one of o-aminophenol, m-aminophenol and p-aminophenol. Preferably, the aminophenol is para-aminophenol. Accordingly, the selective acylation of the aminophenol is the selective acylation of para-aminophenol, thereby resulting in the formation of N-acetyl-para-aminophenol (APAP).

The weight ratio between water and aminophenol in the aqueous solution of aminophenol is in between 1.0:1.0 to 10.0:1.0. Preferably, the weight ratio between water and aminophenol in the aqueous solution of aminophenol is in between 1.0:1.0 to 8.0:1.0, or in between 2.0:1.0 to 6.0:1.0, or in between 3.0:1.0 to 5.0:1.0.

Ketene is used as an acylation reagent in the present invention. Preference here is given to ethenone as the suitable ketene. For the acylation reaction, the weight ratio between the ketene and the aminophenol is in between 0.1:1.0 to 5.0:1.0. Preferably, the weight ratio between the ketene and the aminophenol is in between 0.2:1.0 to 3.0:1.0, or in between 0.3:1.0 to 1.0:1.0, or in between 0.3:1.0 to 0.6:1.0.

Preferably, the reaction step is carried out as follows:
(A) preparing a reaction mixture comprising the aqueous solution of aminophenol and ketene in presence of the catalyst,
(B) heating the reaction mixture to a temperature ranging between 80° C. to 120° C. to obtain a mother liquor, and
(C) optionally repeating the steps (A) to (B) with the mother liquor,
(D) Filtering the mother liquor of step (B) or optionally step (C) to obtain a wet crude comprising an N-acylation product of aminophenol.

Suitable catalyst for the present invention include metal catalyst. For instance, the metal catalyst can be selected from tin, zinc, iron and salts thereof. In the present context, salts include halides (such as chlorides, fluorides, etc.), acetates, nitrates, sulphates, and the like. Preferably, the amount of the catalyst is in between 0.01 wt. % to 5.0 wt. %, or in between 0.1 wt. % to 0.2 wt. % based on the total weight of the reactive mixture.

For the acylation reaction between the aqueous solution of aminophenol and ketene to occur, the reaction mixture is first obtained as outlined in step (A) above. This is achieved using the suitable amounts of water, aminophenol, and ketene, as described herein.

Preferably, the step (A) comprises the following sub steps:
(A1) mixing aminophenol with water in presence of the catalyst and at a temperature ranging between 20° C. to 40° C. to obtain the aqueous solution of aminophenol, and
(A2) mixing ketene with the aqueous solution of aminophenol of step (A1) over a duration of 0.5 h to 5 h and at a temperature ranging between 20° C. to 40° C. to obtain the reaction mixture.

The term "mixing" as used herein, refers to the conventional process of agitating using suitable mixing means known to a person skilled in the art. Such mixing means may be, such as but not limited to, a stirrer. Preferred temperature range in step (A1) is in between 20° C. to 30° C. for obtaining the aqueous solution of aminophenol. Thereafter, ketene is mixed with the aqueous solution of aminophenol over the duration of 0.5 h to 5 h and at temperature ranging between 20° C. to 40° C. to obtain the reaction mixture. Preferably, the duration ranges between 1 h to 3 h and the temperature ranges between 25° C. to 35° C.

In the next step, i.e. step (B), the reaction mixture is heated up to the temperature in between 80° C. to 120° C. to obtain the mother liquor. Preferably, the temperature is in between 80° C. to 100° C. Prior to heating the reaction mixture, suitable amounts of stabilizers can also be added. Such stabilizers can be selected from metal salts, preferably metal sulphurous salts. In the present context, "metal sulphurous salts" refers to sulphurous salts of metals. Suitable metals can be selected from sodium, potassium, lithium, zinc and calcium. Preferably, the metal is sodium. The sulphurous salts can be selected from sulphide ($S_x$), sulphate ($SO_4$), hydrogen sulphate ($HSO_4$), sulphite ($SO_3$), hydrogen sulphite ($HSO_3$), thiosulphate ($S_2O_3$), hydrosulfite ($S_2O_4$), bisulphite ($S_2O_5$), and peroxydisulphate ($S_2O_8$). Typically, the amount of the stabilizer is in between 0.01 wt. % to 5.0 wt. %, or in between 0.25 wt. % to 1.0 wt. % based on the total weight of the reactive mixture. Activated charcoal can also be added here and in similar amounts, i.e. in between 0.01 wt. % to 5.0 wt. %, based on the total weight of the reactive mixture.

The temperature range for step (B), as above, is preferably maintained for a duration ranging between 0.5 h to 5 h, or in between 0.5 h to 2 h. The mother liquor, thus obtained, is optionally recycled to the step (A) and thereafter, to the step (B). This is step (C), also referred as recycling step. Preferably, the mother liquor is recycled at least once to the steps (A) and (B). The recycling of the mother liquor ensures that the yield of the N-acylation product of aminophenol, which has formed due to the acylation reaction, is maximized. The recycling step also ensures that any impurity that has formed during the acylation reaction is minimized and the purity of the N-acylation product of aminophenol increases. These impurities include, but are not limited to, acetic acid, o-acetylated and multi acetylated product and sulphated ash (sulphate salt), which are produced as by-products. Further, any leftover or unreacted aminophenol, ketene, catalyst, stabilizer and activated charcoal that is present in the mother liquor along with the impurities is also recycled to the step (A) for increasing the yield of the N-acylation product of aminophenol and minimize the wastage of the starting materials.

It has been observed that the recycling step (C) advantageously increases the yield and purity of the N-acylation product of aminophenol by ensuring that the amount of the impurities is less than 0.1 wt. %, based on the total weight of the N-acylation product of aminophenol. The recycling step makes the mother liquor saturated with the N-acylation product of aminophenol, thereby increasing its yield.

The mother liquor in step (C) can be subjected to recycling to step (A) and subsequently to step (B) for more than once. For example, the mother liquor is recycled for 2, or 3, or 4, or 5, or 6, or 7, or 8, or 9, or 10 times to step (A). It has been observed that recycling the mother liquor beyond 6 times to step (A) does not improve the yield further. Said otherwise, the yield remains unaffected. The amount of unknown impurities in the isolated N-acylation product of aminophenol, after recycling of the mother liquor is substantially reduced, i.e. less than 0.05 wt. % based on the total weight of the N-acylation product of aminophenol.

Filtration of the mother liquor obtained after several recycling in step (C) results in the wet crude. The wet crude comprises the N-acylation product of aminophenol in increased yield and purity, along with the unknown impurities in amounts less than 0.05 wt. %, based on the total weight of the N-acylation product of aminophenol. The N-acylation product of aminophenol, preferably APAP, in the wet crude is a white colour precipitate.

Preferably, the wet crude in the filtration step (D) is obtained by the following sub-steps:
(D1) filtering the mother liquor of step (C) at a temperature ranging between 90° C. to 95° C. using a filter aid to obtain a filter aid cake and the mother liquor,
(D2) washing the filter aid cake and the mother liquor of step (D1) with preheated water, and
(D3) cooling the mother liquor of step (D2) at a temperature ranging between 15° C. to 40° C. to obtain the wet crude.

Suitable filter aid for filtering the mother liquor include, but not limited to, diatomaceous earth, hyflo supercell and the like. Subsequently, the filter aid cake is washed using preheated water. For this, water is heated to a temperature ranging between 40° C. to 98° C., preferably in between 90° C. to 95° C. After washing, the filter aid cake is cooled slowly to a temperature ranging between 15° C. to 35° C. to obtain the wet crude. Preferably, cooling is carried out at temperature ranging between 20° C. to 30° C. The duration for cooling preferably ranges between 3 h to 10 h, preferably in between 4 h to 8 h. Upon cooling, the wet crude obtained contains precipitates of the N-acylation product of aminophenol.

The pH value of the wet crude is typically maintained at neutral in aqueous medium, i.e. a value of approx. 7.0. In case, the pH value drops or increases beyond 7.0, suitable neutralizing agent is added. Such a neutralizing agent includes inorganic bases, such as sodium or potassium carbonates, bicarbonates, hydroxides; preferably sodium hydroxide (NaOH).

The wet crude in step (D) can be further subjected to step (E), also referred as the recrystallization step. Water, stabilizer and activated charcoal are added during the recrystallization step, followed by heating at temperature ranging between 80° C. to 120° C., preferably in between 90° C. to 95° C. Filtering the wet crude at a temperature ranging between 90° C. to 95° C. using a filter aid as described above and obtaining a filter aid cake. Washing the filter aid cake with preheated water at 90° C. to 95° C. results in the mother liquor containing the N-acylation product of aminophenol, high concentration of water, and traces of acetic acid. Optionally, this mother liquor is recycled back to the step (E), thereby further reducing the acetic acid content in the downstream process steps of filtration and washing. Water is thereafter distilled using suitable means known to the person skilled in the art.

The mother liquor from step (E) is cooled to a temperature ranging between 20° C. to 40° C., preferably in between 20° C. to 30° C. for a duration ranging between 4 h to 8 h, to obtain a slurry of pure N-acylation product of aminophenol. This is subjected to filtration, washing and drying.

Drying is preferably carried under vacuum conditions. Vacuum drying further increases the purity of the N-acylation product of aminophenol. The vacuum drying is carried out at suitable conditions of pressure and temperature. Preferably, the pressure ranges between 50 mbar to 200 mbar and the temperature ranges between 40° C. to 100° C.

For increasing the yield and purity of the N-acylation product of aminophenol, all the process steps described herein are to be performed. If the recycling step (D) is repeated once, as described herein above, the following temporal sequence of steps applies (A)→(B)→(A)→(B)→(D)→(E). If the recycling step is performed twice, the following temporal sequence of steps applies (A)→(B)→(A)→(B)→(A)→(B)→(D)→(E). Similarly, if the recycling step is performed 'n' times, the following temporal sequence of steps applies (A)→(B)→{(A)→(B)}$_n$→(D)→(E). Here, 'n' refers to 1, or 2, or 3, or 4, or 5, or 6, or 7, or 8, or 9, or 10. The effect of the number of recycling on the yield of the N-acylation product of aminophenol is depicted in the example section.

Preferably, the selective acylation of aminophenol, as described herein, is the selective acylation of para-aminophenol or N-acylation of para-aminophenol. Accordingly, the N-acylation product of aminophenol is N-acetyl-para-aminophenol (APAP) or paracetamol.

Advantageously, the process of the present invention is clean and environment-friendly, resulting in high purity and yield for APAP. Additionally, the process is less complex, economical with minimum generation of impurities, as described herein. The impurities generated in the present invention process are quite on much lower concentration as compared to other commercial processes. Ketene being an environmentally-friendly acylation reagent, imparts insertion of —COCH$_3$ group (acyl group) without formation of any by-products as generated with acetic anhydride or acetyl chloride. Moreover, since the reactivity of ketene is quite high, the reaction proceeds at a faster rate and results in almost quantitative conversions with well optimized parameters.

EXAMPLES

The following experimental examples are illustrative of the invention but not limitative of the scope thereof:

| Compounds | |
|---|---|
| Aminophenol | p-aminophenol |
| Ketene | Ethenone |
| Catalyst | Zinc metal |
| Stabilizer | Sodium sulphite (Na$_2$SO$_3$) |
| Activated charcoal | Hyflo ® Super Cel ® |
| Filter media | |
| are available from Sigma Aldrich | |

Preparation of APAP or paracetamol

To a mixture of p-aminophenol (100 g) and 400 ml water under nitrogen atmosphere at 25-30° C. in a 1 L dry flask, the reducing metal catalyst (0.1 g) was added. Ketene gas (42.5 gm) was purged slowly over 1-1.5 h maintaining the temperature around 30° C. with agitation. Catalytic amount of the stabilizer (0.5 to 1.0 gm) and 0.5 wt. % to 1.0 wt. % activated charcoal was added to obtain the reaction mixture. The reaction mixture was then heated in between 90° C. to 95° C. and was maintained for 1 h. Thereafter, the reaction mixture was filtered hot on the filter media and washed with hot water to obtain the mother liquor. The mother liquor was then cooled slowly to 25 to 30° C. and the wet crude was filtered and washed with cold water. The mother liquor and washing were directly used as reaction mixture in next batch of crude paracetamol preparation.

For recrystallization, the wet crude was slurried in 250 ml water. The pH value was adjusted to approx. 7.0 with dilute NaOH solution and thereafter, treated with 0.5 gm of the stabilizer and 1 g of the activated charcoal at 90° C.-95° C. Aqueous mother liquor after hot filtration of the reaction mixture, was treated with approx. 0.25 wt. % to 0.5 wt. % seeding of pure paracetamol and allowed to cool gradually to 25° C. to 30° C. over a period of 5 h to 7 h. The crystalline pure product was filtered, washed with cold water and dried under vacuum at 50° C. to 60° C.

The effect of the number of recycling steps on the yield of pure paracetamol is summarized in Table 1 below.

TABLE 1

No. of recycles and the corresponding yield of paracetamol (APAP)

| Sr. no. | No. of recycles | Batch size (gm) | Water/ mother liquor used for reaction (gm) | Ketene gas (gm) | Acidity of mother liquor (%) | Yield of APAP (%) |
|---|---|---|---|---|---|---|
| 1 | 1 + 0* | 100 | 415 | 44.0 | 3.2 | 92.691 |
| 2 | 1 + 1 | 100 | 415 | 43.0 | 6.0 | 90.673 |
| 3 | 1 + 2 | 100 | 415 | 42.0 | 6.5 | 95.007 |
| 4 | 1 + 3 | 100 | 415 | 42.0 | 7.4 | 96.559 |
| 5 | 1 + 4 | 100 | 415 | 43.0 | 8.4 | 98.721 |
| 6 | 1 + 5 | 100 | 415 | 44.0 | 9.5 | 98.426 |
| 7 | 1 + 6 | 100 | 415 | 43.0 | 11.43 | 98.00 |
| 8 | 1 + 7 | 100 | 415 | 45.0 | 13.20 | 97.75 |
| 9 | 1 + 8 | 100 | 415 | 44.5 | 15.30 | 98.70 |
| 10 | 1 + 9 | 100 | 415 | 43.0 | 16.80 | 97.91 |

*no recycling carried out

As noted in Table 1, the acetic acid content (refer acidity of mother liquor) immediately after the acylation reaction had occurred (refer Sr.no. 1) was significantly lower than the state-of-the-art or commercial processes. The mother liquor containing high amounts of acetic acid (for example Sr.no. 10 or beyond) can be subjected to the recovery step.

The maximum yield of paracetamol was observed when the recycling step was carried out 5 times. It can further be observed here that increasing the number of recycling beyond 5 does not result in any substantial change in the yield.

Table 2 summarizes the analysis of paracetamol for various batches along with the impurities. For the analysis of solubility, the paracetamol obtained using the present invention should be soluble in ethanol (95%) and soluble in acetone, sparingly soluble in water, very slightly soluble in dichloro-methane and ether. For identification purpose, the IR spectra should match the standard IR spectrum. The impurities were determined according to European and Indian pharmacopeia.

TABLE 2

Analysis of paracetamol from several batches

| Parameter | Limit | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| Consistency | As above | Crystalline powder | Crystalline powder | Crystalline powder | Crystalline powder | Crystalline powder | Crystalline powder | Crystalline powder | Crystalline powder | Crystalline powder |
| Colour | As above | White | White | White | White | White | White | White | White | White |
| Solubility | As above | Complies | Complies | Complies | Complies | Complies | Complies | Complies | Complies | Complies |
| Identification | As above | Complies | Complies | Complies | Complies | Complies | Complies | Complies | Complies | Complies |
| *Impurity J -(p-chloro acetanilide) ppm, max | 10 | n.d. | n.d. | n.d. | n.d. | n.d. | n.d. | n.d. | n.d. | n.d. |
| *Impurity K (p-Amino phenol) ppm, max | 50 | 16 | 28 | 21 | 2 | 15 | 7 | 1 | 2 | 3 |
| *Impurity F (p-Nitro phenol) %, max | 0.05 | n.d. | n.d. | n.d. | n.d. | n.d. | n.d. | n.d. | n.d. | n.d. |
| *Any other impurity %, max | 0.05 | BDL | BDL | BDL | BDL | BDL | 0.04 | BDL | 0.01 | 0.01 |
| *Total other impurities %, max | 0.1 | BDL | BDL | BDL | BDL | BDL | 0.04 | BDL | 0.02 | 0.02 |
| *Heavy metals ppm, max | 10 | <10 | <10 | <10 | <10 | <10 | <10 | <10 | <10 | <10 |
| ˆSulphated ash % w/w, max | 0.1 | 0.02 | 0.01 | 0.02 | 0.05 | 0.04 | 0.05 | 0.07 | 0.02 | 0.03 |
| ˆLoss on drying % w/w, max | 0.5 | 0.18 | 0.28 | 0.11 | 0.09 | 0.05 | 0.23 | 0.19 | 0.31 | 0.09 |
| ˆAssay (on dried basis), % w/w, | 99.0 to 101.0 | 100.1 | 100.2 | 100.0 | 100.0 | 99.8 | 99.8 | 100.0 | 100.0 | 99.8 | n.d.—not detected;
BDL—below disregard limit;
*European pharmacopeia;
ˆIndian pharmacopeia As noted above, the paracetamol obtained in accordance with the present invention contains very low amount of impurities without compromising the yield and purity.

The foregoing description of the invention has been set merely to illustrate the invention and is not intended to be limiting. Since the modifications of the disclosed embodiments incorporating the spirit and substance of the invention may occur to the person skilled in the art, the invention should be construed to include everything within the scope of the disclosure.

The invention claimed is:

1. An environment-friendly process for selective acylation of aminophenol comprising reacting an aqueous solution of the aminophenol and a ketene in presence of a catalyst and a stabilizer.

2. The process as claimed in claim 1, wherein a weight ratio between the ketene and the aminophenol is in the range of 0.1:1.0 to 5.0:1.0.

3. The process as claimed in claim 1, wherein the aminophenol is para-aminophenol.

4. The process as claimed in claim 1, wherein the ketene is ethenone.

5. The process as claimed in claim 1, wherein the reaction is carried out by:

(A) preparing a reaction mixture comprising the aqueous solution of the aminophenol and ketene in presence of the catalyst and the stabiliser,
(B) heating the reaction mixture to a temperature ranging between 80° C. to 120° C. to obtain a mother liquor, and
(C) optionally repeating (A) to (B) with the mother liquor,
(D) Filtering the mother liquor of (B) or optionally (C) to obtain a wet crude comprising an N-acylation product of the aminophenol.

6. The process as claimed in claim 5, further comprising:
(E) Recrystallizing, washing and drying the wet crude of step (D) to obtain a purified N-acylation product of the aminophenol.

7. The process as claimed in claim 1, wherein the catalyst is a metal catalyst selected from a group consisting of tin, zinc, iron and salts thereof.

8. The process as claimed in claim 1, wherein the stabilizer is a metal sulphurous salt containing metals and sulphurous salts, said metals being selected from a group consisting of sodium, potassium, lithium, zinc and calcium, and sulphurous salts being selected from a group consisting of sulphide ($S_x$), sulphate ($SO_4$), hydrogen sulphate ($HSO_4$), sulphite ($SO_3$), hydrogen sulphite ($HSO_3$), thiosulphate ($S_2O_3$), hydrosulphite ($S_2O_4$), bisulphite ($S_2O_5$), and peroxydisulphate ($S_2O_8$).

9. The process as claimed in claim 1, wherein the selective acylation of the aminophenol is the selective acylation of para-aminophenol to obtain N-acetyl-para-aminophenol.

10. The process as claimed in claim 5, wherein the N-acylation product of the aminophenol comprises impurities less than 0.05 wt. % based on a total weight of the N-acylation product of the aminophenol.

* * * * *